US00PP13014P2

(12) United States Plant Patent
Fuess

(10) Patent No.: US PP13,014 P2
(45) Date of Patent: Sep. 24, 2002

(54) CHRYSANTHEMUM PLANT NAMED 'EMPIRE COURTNEY'

(75) Inventor: Janet S. Fuess, New York Mills, NY (US)

(73) Assignee: Yoder Brothers, Inc., Barberton, OH (US)

( * ) Notice: Subject to any disclaimer, the term of this patent is extended or adjusted under 35 U.S.C. 154(b) by 2 days.

(21) Appl. No.: 09/837,586

(22) Filed: Apr. 19, 2001

(51) Int. Cl.[7] ..... A01H 5/00
(52) U.S. Cl. ..... Plt./297
(58) Field of Search ..... Plt./297, 286

*Primary Examiner*—Bruce R. Campell
*Assistant Examiner*—June Hwu
(74) *Attorney, Agent, or Firm*—C. A. Whealy

(57) ABSTRACT

A distinct cultivar of Chrysanthemum plant named 'Empire Courtney', characterized by its upright plant habit; freely branching growth habit; uniform and freely flowering habit; daisy-type inflorescences; and lavender pink-colored ray florets.

1 Drawing Sheet

BOTANICAL CLASSIFICATION

*Chrysanthemum×morifolium.*

VARIETY DENOMINATION

'Empire Courtney'.

BACKGROUND OF THE INVENTION

The present invention relates to a new and distinct cultivar of Chrysanthemum plant, botanically known as *Chrysanthemum×morifolium* and hereinafter referred to by the name 'Empire Courtney', The new cultivar is a product of a planned breeding program conducted by the Inventor in New Hartford, N.Y. The objective of the breeding program is to create new garden-type Chrysanthemum cultivars having inflorescences with desirable inflorescence forms, attractive floret colors and good garden performance.

The new Chrysanthemum originated from a cross made by the Inventor in October, 1995, in New Hartford, N.Y., of the Chrysanthemum cultivar Empire Crown Jewel, disclosed in U.S. Plant Pat. No. 9,738, as the female, or seed, parent with a Chrysanthemum proprietary seedling selection identified as code number H94-2, as the male, or pollen, parent. The new Chrysanthemum was discovered and selected by the Inventor as a single flowering plant within the progeny of the stated cross grown in a controlled environment in New Hartford, N.Y. in September, 1996. The selection of this plant was based on its desirable inflorescence form, attractive ray floret color and good garden performance.

Asexual reproduction of the new cultivar by terminal cuttings taken in a controlled environment in New Hartford, N.Y. since October, 1996, has shown that the unique features of this new Chrysanthemum are stable and reproduced true to type in successive generations.

SUMMARY OF THE INVENTION

The cultivar Empire Courtney has not been observed under all possible environmental conditions. The phenotype may vary somewhat with variations in environment such as temperature, daylength and light intensity, without, however, any variance in genotype.

The following traits have been repeatedly observed and are determined to be the unique charateristics of 'Empire Courtney'. These characteristics in combination distinguish 'Empire Courtney' as a new and distinct cultivar:

1. Upright and mounded plant habit.
2. Freely branching, dense, full plants.
3. Uniform and freely flowering.
4. Daisy-type inflorescences.
5. Lavender pink-colored ray florets.

Plants of the new Chrysanthemum can be compared to plants of the female parent, the cultivar Empire Crown Jewel. In side-by-side comparisons conducted in Salinas, Calif., plants of the new Chrysanthemum differ from plants of the cultivar Empire Crown Jewel in the following characteristics:

1. Plants of the new Chrysanthemum are more compact and bushier than plants of the cultivar Empire Crown Jewel.
2. Plants of the new Chrysanthemum have larger inflorescences than plants of the cultivar Empire Crown Jewel.
3. Ray floret color of plants of the new Chrysanthemum is lighter than ray floret color of plants of the cultivar Empire Crown Jewel.

Compared to plants of the male parent, plants of the new Chrysanthemum differ in ray floret color.

Plants of the new Chrysanthemum can be compared to plants of the cultivar Felicia, disclosed in U.S. Plant Pat. No. 9,809. In side-by-side comparisons conducted in Salimas, Calif., plants of the new Chrysanthemum differ from plants of the cultivar Felicia in the following characteristics:

1. Plants of the new Chrysanthemum are more mounded in plant habit than plants of the cultivar Felicia.
2. Plants of the new Chrysanthemum have larger inflorescences than plants of the cultivar Felicia.
3. Plants of the new Chrysanthemum flower about three weeks later than plants of the cultivar Felicia.
4. Ray floret color of plants of the new Chrysanthemum is lighter than ray floret color of plants of the cultivar Felicia.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph at the top of the sheet comprises a side perspective view of a typical flowering plant of 'Empire Courtney'.

The photograph at the bottom of the sheet comprises a close-up view of typical inflorescences of the cultivar 'Empire Courtney'.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate those generally used in commercial garden Chysanthemum production. One rooted cutting was planted in a 15-cm container in July, 2000 and plants were grown under natural season conditions. Plants were not pinched, that is, the terminal apex was not removed to enhance branching. Measurements and numerical values represent averages for typical flowering plants.

Commercial classification: Daisy-type garden Chrysanthemum.

Parentage:

*Female, or seed, parent.*—*Chrysanthemum*× *morifolium* cultivar Empire Crown Jewel, disclosed in U.S. Plant Pat. No. 9,738.

*Male, or pollen, parent.*—*Chrysanthemum*×*morifolium* proprietary seedling selection identified as code number H94-2, not patented.

Propagation:

*Type.*—Terminal tip cuttings.

*Time to initiate roots.*—About four days at 21° C.

*Time to produce a rooted cutting.*—About ten days at 21° C.

*Root description.*—White, fine and fibrous.

*Rooting habit.*—Freely branching.

Plant description:

*Appearance.*—Perennial herbaceous daisy-type garden Chrysanthemum. Inverted triangle; upright plant form. Stems initially upright, then slightly outwardly spreading giving a uniformly mounded appearance to the plant. Freely branching with about 9 lateral branches per plant.

*Plant height.*—About 32 cm.

*Plant diameter.*—About 36 cm.

*Lateral branches.*—Length: About 26 cm. Diameter: About 5 mm. Internode length: About 2 cm. Aspect: Mostly upright. Texture: Pubescent. Color: 146A overlain with anthocyanin, close to 59A.

*Foliage description.*—Leaf arrangement: Alternate. Length: About 5.8 cm. Width: About 4.7 cm. Apex: Cuspidate to mucronate. Base: Attenuate. Margin: Palmately lobed, sinuses mostly divergent. Texture: Both surfaces, pubescent; veins prominent on lower surface. Color: Young foliage upper surface: 147A. Young foliage lower surface: 147B. Mature foliage upper surface: 147A. Mature foliage lower surface: 147B. Venation, both surfaces: 147B. Petiole length: About 1.5 cm. Petiole diameter: About 2.5 mm. Petiole color, both surfaces: 146C.

Inflorescence description:

*Appearance.*—Daisy-type inflorescence form with elongated oblong-shaped ray florets. Inflorescences borne on terminals above foliage, arising from leaf axils. Disc and ray florets arranged acropetally on a capitulum. About 14 inflorescences per lateral; about 126 inflorescences per plant.

*Flowering response.*—Under natural season conditions, plants flower in early October in the Northern Hemisphere and continue to flower for at least three weeks depending on weather conditions.

*Inflorescence bud* (*before showing color*).—Height: About 5.5 mm. Diameter: About 7 mm.

*Inflorescence size.*—Diameter: About 5.3 cm. Depth (height): About 2.2 cm. Disc diameter: About 1.1 cm. Receptacle diameter: About 5 mm.

*Ray florets.*—Shape: Elongate oblong. Length: About 2.9 cm. Corolla tube length: About 3 mm. Width: About 8 mm. Apex: Acute, emarginate or dentate. Margin: Entire. Texture: Smooth, glabrous, satiny. Orientation: Intially upright and incurved, then perpendicular to the peduncle and concave. Number of ray florets per inflorescence: About 39 in about two to three rows. Color: When opening, upper surface: 75A to 77C with 77A to 77B overtones. When opening, lower surface: 75A to 77C. Opened inflorescence, upper surface: 75A to 77C with 77A to 77B overtones; with subsequent development, 77D with 77A to 77C overtones, eventually faint to white, close to 155D, with 77A to 77D overtones. Opened inflorescence, lower surface: 77C to 77D.

*Disc florets.*—Shape: Tubular, apex dentate. Length: About 6 mm. Width: Apex: About 2 mm. Base: About 1 mm. Number of disc florets per inflorescence: About 94. Color: Immature: 144A to 154A. Mature: Apex: 9A. Mid-section and base: 155D.

*Phyllaries.*—Size: Length about 5 mm. and width about 1 mm. Color: 143A.

*Peduncle.*—Aspect: Flexible, angled about 30° from the stem. Length: First peduncle: About 5.7 cm. Fourth peduncle: About 9.1 cm. Diameter: About 2.5 mm. Texture: Pubescent. Color: 144A.

*Reproductive organs.*—Androecium: Present on disc florets only. Anther color: 9A. Pollen: Moderate. Pollen color: 13A to 15A. Gynoecium: Present on both ray and disc florets.

*Seed.*—Seed production has not been observed.

Disease resistance: Plants of the new Chrysanthemum have not been shown to be resistant to pathogens common to Chrysanthemums.

Garden performance: Plants of the new Chrysanthemum have been observed to be tolerant to temperature 0–40° C., rain and wind.

It is claimed:

1. A new and distinct cultivar of Chrysanthemum plant named 'Empire Courtney', as illustarted and described.

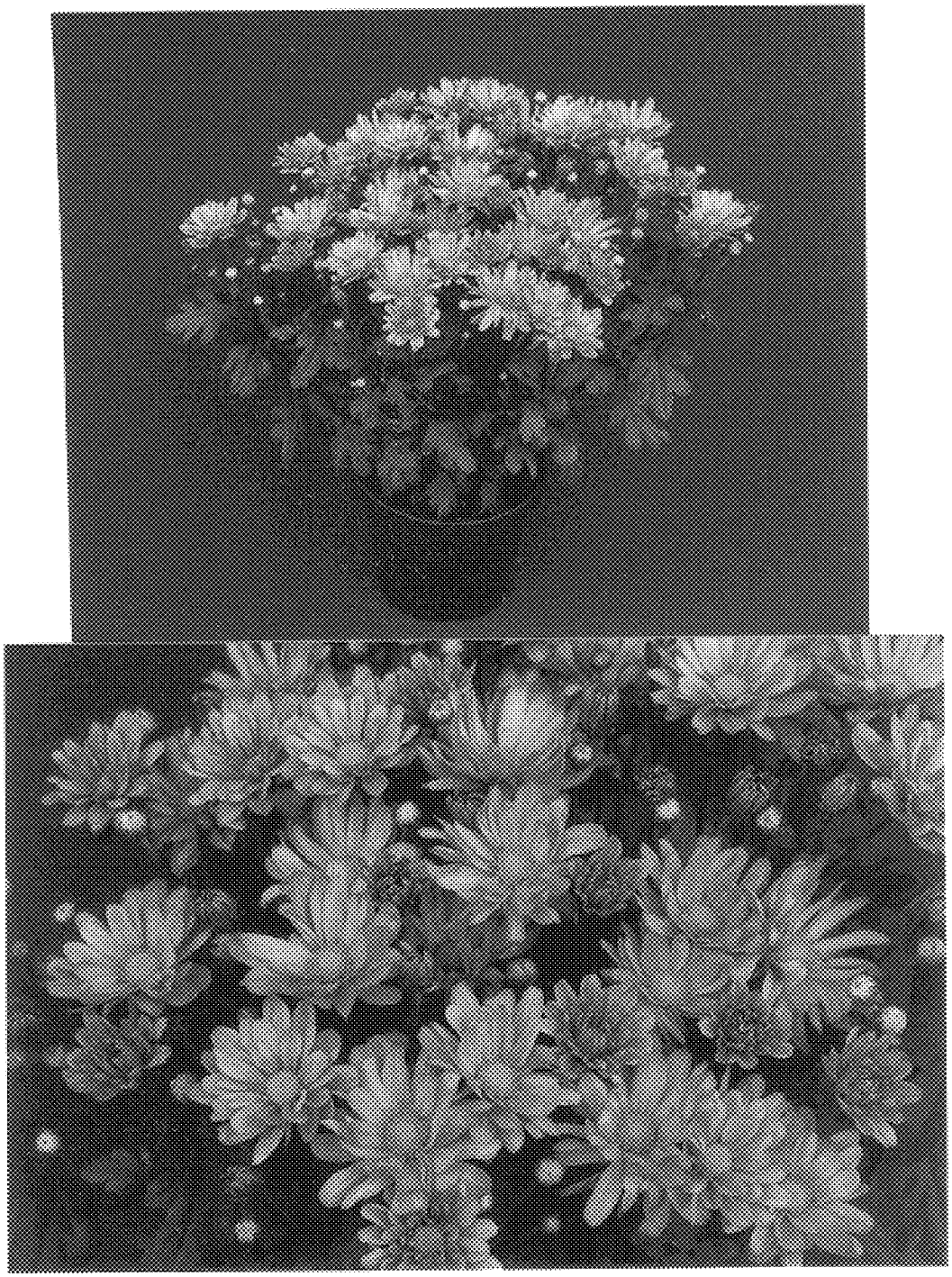

* * * * *